United States Patent [19]

Tsao et al.

[11] 4,281,063

[45] * Jul. 28, 1981

[54] PROCESS FOR TREATING CELLULOSIC MATERIALS AND OBTAINING GLUCOSE THEREFROM

[75] Inventors: George T. Tsao; Michael R. Ladisch; Christine M. Ladisch, all of West Lafayette, Ind.; Teh-An Hsu, Honolulu, Hi.

[73] Assignee: Purdue Research Foundation, West Lafayette, Ind.

[ * ] Notice: The portion of the term of this patent subsequent to Nov. 20, 1996, has been disclaimed.

[21] Appl. No.: 81,537

[22] Filed: Oct. 3, 1979

Related U.S. Application Data

[63] Continuation-in-part of Ser. No. 884,479, Mar. 8, 1978, abandoned.

[51] Int. Cl.³ .......................... C13K 1/02; C12P 19/14
[52] U.S. Cl. ...................................... 435/99; 127/37; 536/56
[58] Field of Search ............... 127/37; 435/99; 536/56

[56] References Cited

U.S. PATENT DOCUMENTS

| | | | |
|---|---|---|---|
| 2,302,022 | 11/1942 | Giordani | 127/37 |
| 2,465,347 | 3/1949 | Boehm | 127/37 |
| 3,212,933 | 10/1965 | Hess | 127/37 |
| 3,972,775 | 8/1976 | Wilke | 435/99 |

Primary Examiner—Sidney Marantz
Attorney, Agent, or Firm—John R. Nesbitt; Robert E. Harris

[57] ABSTRACT

A process for treating cellulosic materials to obtain glucose therefrom, which process includes an initial acid or base treatment of the cellulosic materials to remove hemicellulose, followed by a solvent treatment of the solid residue to dissolve the native cellulose contained therein. The dissolved cellulose is separated from the solid lignin-containing residue, whereafter the cellulose is reprecipitated by contacting the solution thereof with water. The reprecipitated cellulose is hydrolyzed to glucose either by acid or enzyme hydrolysis. If desired, the cellulose may be reprecipitated and hydrolyzed in the presence of the lignin-containing solid, the latter being separated from the glucose.

17 Claims, 3 Drawing Figures

PROCESS FOR TREATING CELLULOSIC MATERIALS AND OBTAINING GLUCOSE THEREFROM

RELATED APPLICATION

This application is a continuation-in-part of Ser. No. 884,479, filed on Mar. 8, 1978, now abandoned.

FIELD OF THE INVENTION

This invention relates to a process for treating cellulosic materials, and, more particularly, to an improved process for yielding glucose from cellulosic materials.

BACKGROUND OF THE INVENTION

The utilization of cellulosic waste materials, such as cornstalks, sawdusts, straws, bagasse, and the like, has been the subject of strong interest recently, particularly with respect to utilization of such waste materials for developing alternate sources of fuels, chemicals and other useful products.

It is known that cellulosic materials include three principal components—cellulose, hemicellulose, and lignin. Methods for extraction of hemicellulose have heretofore been suggested and/or utilized and such extracted hemicellulose can be utilized for many existing methods involving hydrolysis, fermentation, pyrolysis and the like.

Lignin has likewise heretofore been isolated from cellulosic materials. Lignin has been found to be higher in hydrogen and carbon and lower in oxygen content than cellulose and hemicellulose and has the highest heating value of the three. Isolated lignin can be burnt directly to generate steam and electricity and can also be used to produce a number of useful products including vanillin, dimethylsulfoxide, dimethyl sulfide, methyl mercaptan, and catechol.

Recovery of cellulose and/or utilization of the same as by acid or enzyme hydrolysis to provide glucose has presented a problem, however, primarily due to the highly ordered crystalline structure of the cellulose molecules and to the presence therein of a lignin seal. Thus, when employing prior art acid hydrolysis processes, it has been necessary to use rather rigorous conditions such that unacceptably low yields of glucose are obtained along with correspondingly large amounts of glucose decomposition products. This generally undesirable result can be appreciated more fully when considering acid hydrolysis as involving the following sequential reaction:

$$A \xrightarrow{k_1} B \xrightarrow{k_2} C$$

where A is cellulose, B is glucose, and C is undesirable side products. Reports on the acid hydrolysis of woods, based on research conducted during World War II by J. F. Saeman of the U.S. Forrest Products Laboratory, states that the rate of $$A \xrightarrow{k_1} B$$

is about the same as $$B \xrightarrow{k_2} C.$$

In other words the formation of side products from glucose occurred at about the same rate as formation of glucose from cellulose. Consequently, the maximum glucose level in the hydrolysate was only 20-30% of the glucose potentially available from the cellulose. Over the years some improvements in yields have been obtained by reducing reaction times, increasing temperature and pressure, and modifying processing equipment. Yet with all these improvements, the best yields obtained to date, using this "conventional" technology, are less than 60%.

Prior art processes which employ enzyme hydrolysis, have resulted in significantly higher yields of glucose with almost no by-product formation. However, because the enzymes can not themselves break or degrade the lignin seal, it is necessary to macerate or grind the raw cellulosic material to a very considerable degree to make enzyme hydrolysis more effective. Obviously, such grinding requires significant amounts of energy which adds to the cost and reduces the attractiveness of enzyme hydrolysis processes.

SUMMARY OF THE INVENTION

Accordingly, it is an object of this invention to provide an improved process for obtaining glucose from cellulosic materials.

It is another object of this invention to provide a process for obtaining glucose from cellulosic materials, which include hydrolyzing cellulosic materials to yield glucose and subsequently removing lignin from the glucose.

It is yet another object to provide a process for fractionating cellulosic materials into its component parts, and to separate the lignin portion therefrom prior to hydrolyzing the cellulose portion to glucose.

It is yet another object of this invention to provide an improved process for recovering cellulose in an easily hydrolyzable form from cellulosic materials.

It is another object of this invention to provide an improved process for recovering cellulose from cellulosic materials that includes fractionation of said cellulosic materials.

It is yet another object of this invention to provide a process for recovery of cellulose and hydrolyzing said recovered cellulose to provide glucose.

The above and other objects and advantages are achieved in accordance with the process of the present invention by transforming the cellulose component of a crude cellulosic material into a form which is more readily hydrolyzable to glucose by a factor of from about 5 to about 20 fold, as compared to the reaction rate of the native cellulose component in the cellulosic material. The process includes a preliminary treatment of the cellulosic material with either a dilute acid or base to separate the hemicellulose portion thereof from the cellulose and lignin portions, followed by a solvent treatment which degrades the lignin seal and dissolves the cellulose. The cellulose may then be separated from the solid lignin-containing residue, whereafter the cellulose is reprecipitated in a less structured or amorphous form which is much more readily hydrolyzable to glucose than is the native, structured cellulose in the original cellulosic material. If desired, the dissolved cellulose may be reprecipitated and hydrolyzed to glucose in the presence of the lignin-containing residue, whereafter the solid lignin is removed from the glucose.

With the foregoing in view, it will become apparent to one skilled in the art as the description proceeds, that this invention resides in the novel process substantially as hereinafter described, and more particularly defined by the appended claims, and that changes in the precise embodiments of the herein disclosed invention are meant to be included as coming within the scope of the claims.

BRIEF DESCRIPTION OF THE DRAWING

The invention is illustrated in the accompanying drawing wherein.

DESCRIPTION OF THE INVENTION

As suggested hereinabove, cellulosic materials comprise hemicellulose and cellulose molecules in the form of highly ordered crystalline structures. In addition, lignin is present in the cellulosic material, at least in part, as a physical seal surrounding and interpenetrating the cellulose crystalline structures.

In one embodiment of the process of this invention, selective solvent extraction is utilized to fractionate hemicellulose, cellulose and lignin (the three major components of all cellulosic materials). This fractionation is desired since it has been found that after cellulose is dissolved in solution, the impediments to hydrolysis of the cellulose have been removed. It is hypothesized that the impediments to cellulose hydrolysis are the crystalline structure of the cellulose molecules and the lignin seal surrounding and interpenetrating the crystalline cellulose molecules. The cellulose which is recovered during the fractionation is readily hydrolyzable and can, therefore, be used as a source of glucose.

Figure 1:
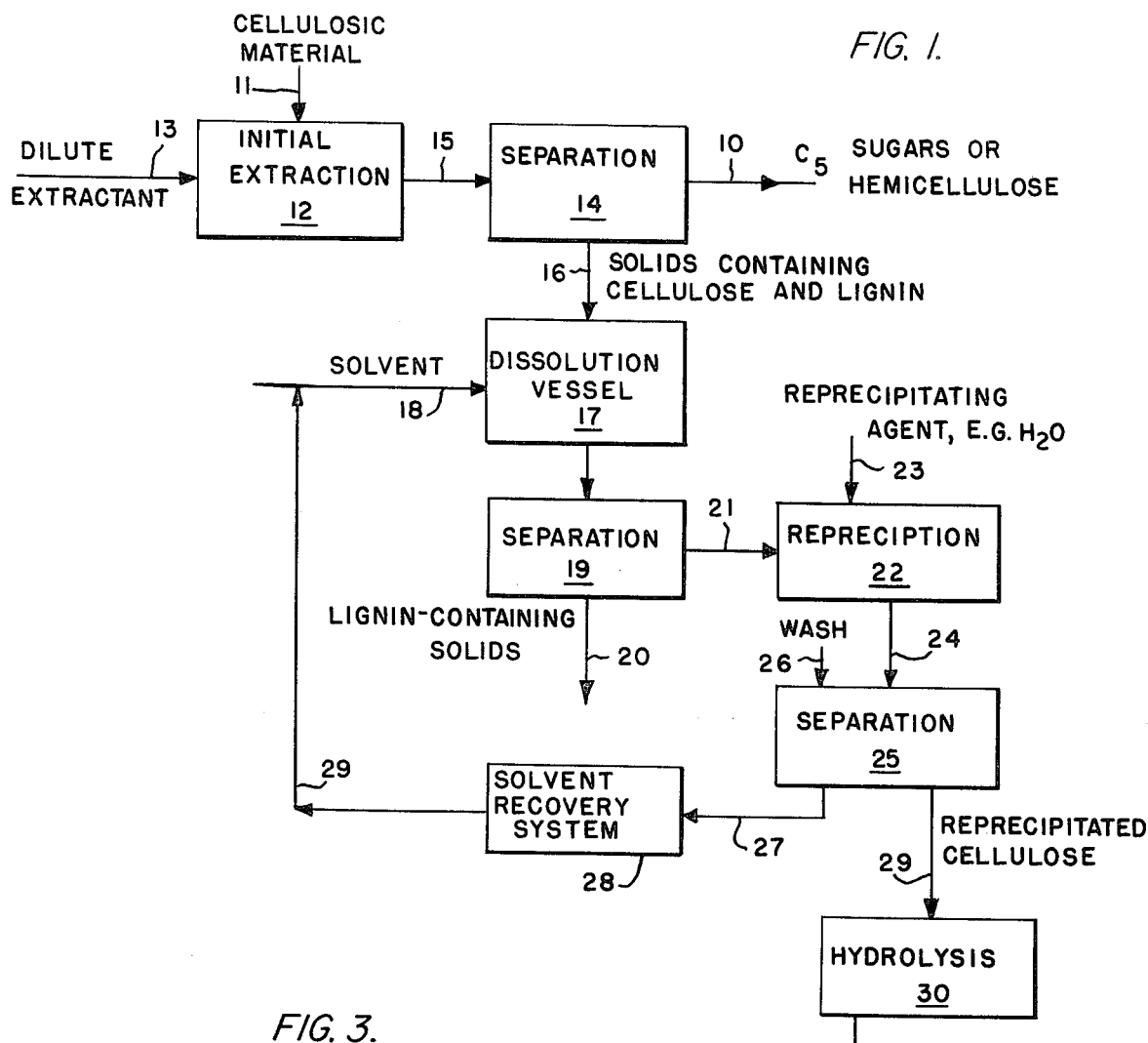
FIG. 1 is a flow diagram illustrating a particular mode of operation of the cellulose conversion process of the present invention, wherein lignin-containing solids are separated from dissolved cellulose prior to reprecipitation of the cellulose.

Referring now to the drawing, and more particularly to FIG. 1, there is shown a schematic flow sheet of one embodiment of the invention wherein a cellulosic material, such as corn stalks, bagasse or the like, after being physically reduced, if necessary or desired, to a suitable size, for example, from about 5 mesh or larger to about 100 mesh, is introduced through line 11 into a suitable hydrolysis or extraction tank 12. In the tank 12, the cellulosic material is treated under mild conditions with either dilute acid or base which is introduced into the tank through line 13. This step, which involves well known reaction conditions (typically 0.5-5% $H_2SO_4$ at about 90°-140° C. for 15 to 300 minutes) fractionates the cellulosic material into a liquid fraction and a solid fraction, both of which are passed through line 15 to separator 14. The liquid fraction, which is removed from the separator through line 10 contains predominately either $C_5$ sugars (when a dilute acid extraction is performed in tank 12) or hemicellulose (when a dilute basic extraction is performed), whereas the solid fraction contains the native crystalline cellulose and lignin portions of the cellulosic material. The solid fraction is passed through line 16 to a dissolution vessel 17 to which a suitable cellulose solvent is added through line 18.

There are a number of solvents reported in literature capable of dissolving cellulose and any one of these available solvents may be employed. For example, the solvent added through line 18 may comprise a quaternary ammonium base, such as benzyltrimethylammonium hydroxide; and aprotic solvent, such as dimethyl sulfoxide-para-formaldehyde, nitrosylics, sulfur oxides, and oxychlorides; a strong mineral acid; or a metal complex, such as cupriethylene diamine, Cadoxen, Zinzoxen or the like.

The relative amount of solvent added to vessel 17 per weight of solids can vary widely, and amounts ranging from as little as about 0.1 weight of solvent per weight of solids to about 20 weights of solvent per weight of solids have been found to be satisfactory. However, as will be discussed more fully hereinbelow, it is generally preferred to employ from about 0.1 to about 10 weights of solvent per weight of solids when the lignin portion of the cellulosic material is to be separated after the cellulose is hydrolyzed to glucose (FIG. 2), and from about 10 to about 20 weights of solvent per weight of solids when the lignin portion is to be removed before the cellulose is hydrolyzed to glucose (FIG. 1). The dissolution of the cellulose in vessel 17 generally is conducted at ambient temperature, but temperatures ranging from about $-35°$ C. to 35° C. would suffice. The period of contact between the cellulose solvent and the solids may vary widely, for example, from as short as about one-half hour to as long as about three months.

For the purpose of illustration, the embodiment of the invention shown in FIG. 1 is described in connection with the use of Cadoxen as the cellulose solvent. However, as indicated above, the invention is not so limited and the use of other cellulose solvents is contemplated.

Cadoxen, which was first reported by Jayme and Neuschaffer (Jayme, G. and Neuschaffer, K., 1957 *Die Naturwissenschaften*, 44 (3): 62–63, and Jayme, G. and Neuschaffer, K., 1957 *Die Makromolekulare Chemie*, 28:71–83), is made of 25–30% ethylenediamine and 70–75% water, and also about 4.5 to 7% cadmium (added as oxide or hydroxide). Cadoxen has good solvating properties, is a clear, colorless, nearly odorless liquid, is stable for an almost unlimited time, causes little degradation of cellulose and is relatively easy to prepare.

The fact that water is a part of Cadoxen formulation is desirable since most cellulosic wastes contain moisture. Thus, Cadoxen requires no pre-drying of the cellulosic wastes, which avoids an otherwise costly operation.

Referring again to FIG. 1, from about 0.1 to about 20 and preferably from about 10 to 20 parts by weight of Cadoxen is added to the dissolution vessel 17 per part by weight of solids to effect the dissolution of the cellulose. This results in the formation of slurry which can be separated by filtration, centrifugation or the like in separator 19 into a cellulose-solvent solution and a lignin-containing solid residue. The lignin-containing residue is removed from the separator 19 through line 20 and is either discarded as waste or processed as desired, such further treatment, if any, forming no part of this invention.

The cellulose-solvent solution which is removed from the separator 19 through line 21 is physically stable but this stability apparently requires a close balance among cellulose, water, ethylenediamine and cadmium. The exact nature of the balance is not precisely known, but if, for example, excess water is added, cellulose will reprecipitate from the solution. The addition of from about 1 to about 10 volumes acetone or an alcohol, such as ethanol or methanol, per volume of cellulose-solvent will also cause reprecipitation. Cadoxen is of high pH, and upon addition of an acid, cellulose also reprecipitates from the solution. The reprecipitated cellulose is amorphous in nature, as compared to the ordered crystalline structure of native cellulose and is much more susceptible to hydrolysis. However, on standing for as little as a few hours, the reprecipitated cellulose will revert to the crystalline form, unless it is stored either at a high pH (greater than about 11) or a low pH (lower than about 5).

In order to take advantage of the greater susceptibility of the amorphous reprecipitated cellulose to hydrolysis, the cellulose-solvent removed from the separator 19 is introduced into a reprecipitor vessel 22, along with from about 1 to 10 volumes of $H_2O$, acid or alcohol as a reprecipitating agent. The reprecipitating agent, preferably water, is introduced into the reprecipitator vessel through line 23.

Figure 3:
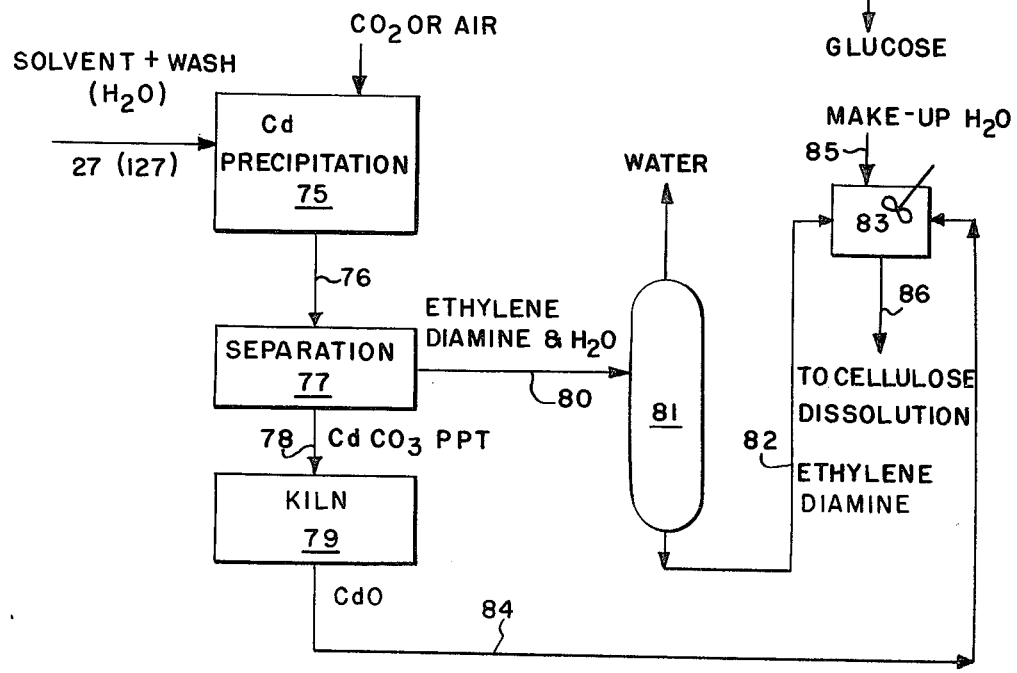
FIG. 3 is a flow diagram illustrating one mode of operation of the solvent recycle system contemplated by this invention.

The solvent, reprecipitating agent and amorphous cellulose precipitate are withdrawn from the reprecipitator vessel through line 24 and are introduced into a centrifuge, filter or other suitable separator 25 where the reprecipitated cellulose is recovered and preferably washed, for example, with water introduced into the separator through line 26. The solvent, reprecipitating agent and wash water are removed from the separator through line 27 and may be discarded. However, in order to improve the economics of the process, the solvent should be recovered and reused. Accordingly, the solvent, reprecipitating agent and wash water are withdrawn from the separator and sent to a solvent recovery system 28. The solvent recovery system is discussed more fully hereinbelow in connection with FIG. 3.

The reprecipitated cellulose is then passed through line 29 to a suitable tank or vessel 30 where it is hydrolyzed to glucose by known acid or enzyme technology using, for example, dilute sulfuric acid or a cellulase enzyme solution (most likely an endo-1, 4-beta-glucanase and other celluloytic enzymes, such as obtained from *Trichoderma viride*; either free or immobilized) as the hydrolytic agent.

Figure 2:
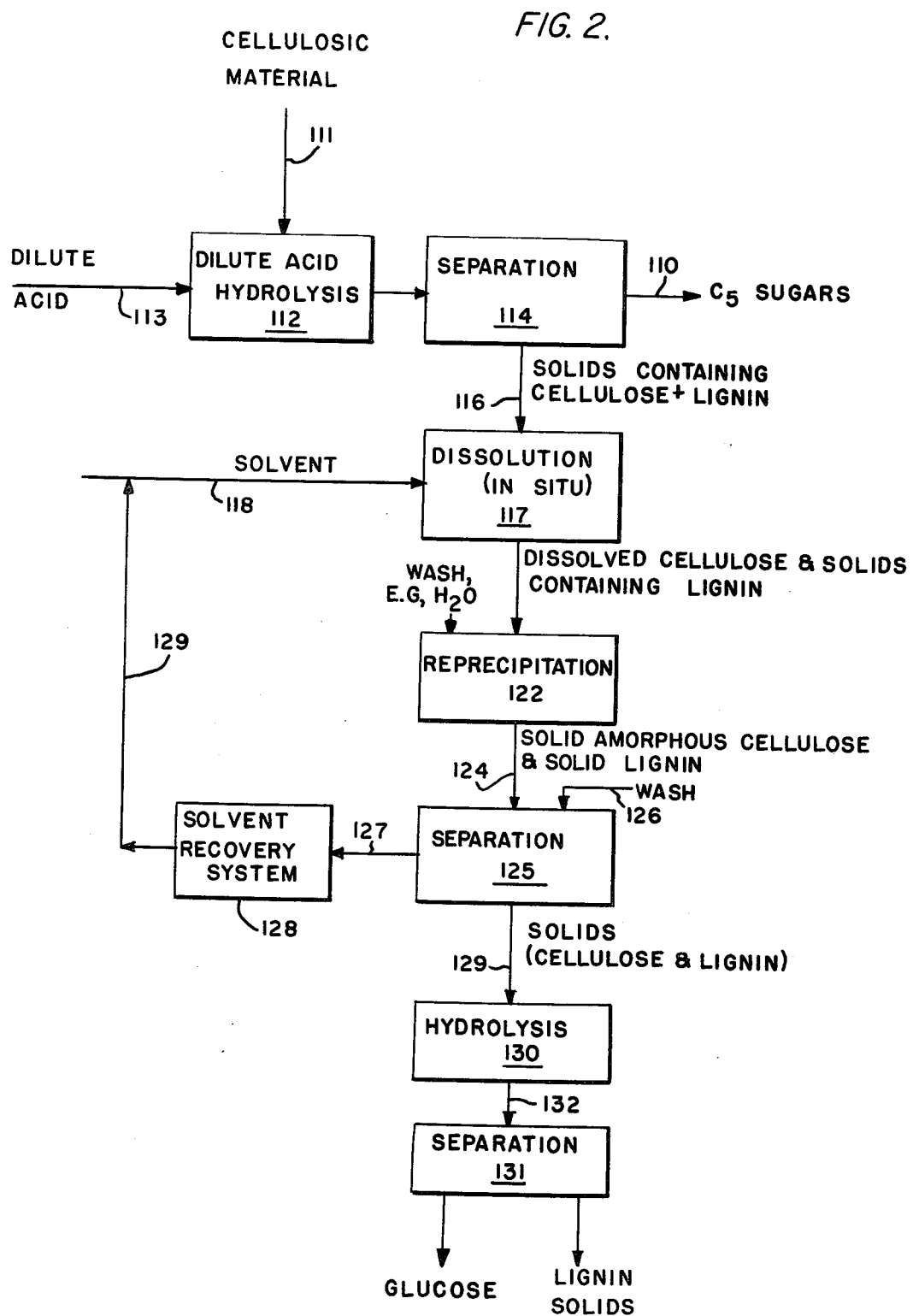
FIG. 2 is a flow diagram of another mode of operation, wherein the dissolved cellulose is reprecipitated and hydrolyzed in the presence of the lignin-containing solids.

In a further embodiment of the process of our invention, which is illustrated in FIG. 2, cellulose is dissolved and reprecipitated "in situ," i.e., in the presence of the solid lignin-containing residue. In other words, the cellulose-solvent is not separated from the lignin-containing solid residue before the cellulose is reprecipitated in amorphous form. In fact, the lignin is not removed from the process until after the cellulose is hydrolyzed to glucose.

Referring now to FIG. 2, it will become evident that this embodiment involves many of the same process steps as the previously described embodiment. Accordingly, the process equipment in FIG. 2 is designated with numbers corresponding to the equipment in FIG. 1, except that the numbers are higher by one hundred. For example, the line through the cellulose material is entered into the initial extraction vessel 12 in FIG. 1 is designated as line 11, whereas the corresponding vessel and line in FIG. 2 are designated 112 and 111, respectively.

In this embodiment, the process steps can be the same as in connection with the embodiment of FIG. 1 through the dissolution of the cellulose in vessel 117. However, as indicated above, the "in situ" dissolution generally utilizes somewhat less solvent, for example, from about 0.1 to 10 parts by weight solvent per part by weight solids, as opposed to the preferred range of from about 10 to 20 parts by weight solvent per part by weight solids for the previously described embodiment. After the dissolution step, however, the embodiments differ slightly because the separator 19 is eliminated and both the lignin-containing solids and the cellulose-solvent are fed to the reprecipitator vessel 122. Thus, the solids introduced to the hydrolysis vessel 130 through line 129 contain both the reprecipitated cellulose and the lignin, the latter being separated from the glucose by filtration, centrifugation or the like in separator 131 after the enzyme or acid hydrolysis of the cellulose has taken place in the presence of the lignin.

In order to improve the economics of the process, the solvent, Cadoxen in the case of the disclosed embodiments, needs to be recovered and reused. By different recycle techniques, the process can be further divided into a number of alternatives. For example, referring to FIG. 3, the spent solvent, reprecipitating agent and wash water withdrawn from the separator 25 (or 125) through line 27 (or 127) may be treated with carbon dioxide or air in a suitable vessel 75 to precipitate the cadmium portion of the solvent as cadmium carbonate or cadmium hydroxide or mixture thereof. The resulting slurry may be introduced through line 76 into a suitable separator 77 wherein the cadmium carbonate or cadmium hydroxide or mixture thereof precipitate is separated from the ethylene diamine portion of the solvent and the reprecipitating agent and wash water. The precipitate is then introduced through line 79 into a kiln 79 where it is regenerated to cadmium oxide by heating to about 250° to 350° C.

The liquid material removed from the separator 77 is passed through line 80 to a standard distillation or extraction column or evaporator 81 wherein the ethylene diamine and water (and alcohol or acetone, if these materials are used as the reprecipitating agent) are separated. The separated ethylene diamine is removed from the column 81 and is fed through line 82 to a mixing vessel 83 where it is mixed with the cadmium oxide from the kiln 79 and make-up water to regenerate the Cadoxen, the cadmium oxide being introduced into the mixing vessel 83 through line 84 and the make-up water being introduced therein through line 85. The regenerated Cadoxen is then withdrawn from the mixing vessel through line 86 for addition to the solvent in line 18 (FIG. 1) or 118 (FIG. 2).

Alternative procedures for regenerating the Cadoxen solvent may be enumerated as follows:

(a) Adding $CO_2$ directly into a cellulose-Cadoxen solution whereupon both cellulose and cadmium carbonate will precipitate. After separation from the liquid which contains ethylenediamine that is to be recovered, for example, as in FIG. 3, the mixture of the two solid precipitates can be treated with cellulases to hydrolyze and dissolve away cellulose to produce glucose. The cadmium carbonate precipitate left behind can be converted into cadmium oxide for reuse; and (b) Adding a water immicible solvent to the cellulose-Cadoxen solution to extract ethylenediamine for recycle, and to precipitate the cellulose. This procedure will, in one step, separate the mixture into three fractions: amine in an organic layer, cadmium in an aqueous layer and cellulose as a precipitate. The three fractions can be processed separately, generally in accordance with the principles outlined herein.

The following examples are illustrative of the invention:

EXAMPLE 1

(a) Preparation of the Solvent (Cadoxen)

Ethylene diamine, 25 to 30% in water, was saturated by adding an excess of cadmium oxide which was previously oven dried. Cadmium oxide which did not dissolve formed a hydroxide which appeared as a white precipitate. The precipitate was filtered off. The procedure of adding cadmium oxide and separating out the hydroxide was performed twice to insure that a solution saturated with cadmium oxide resulted. In this way an aqueous solution of 25 to 30% ethylenediamine and 4.5 to 7% cadmium resulted. Due to its cadmium and ethylene diamine content, this solvent is commonly known as Cadoxen.

(b) Dissolution of α-Cellulose (I) Crystalline α-cellulose (Avicel, obtained from FMC), 0.1 g, was added to and mixed with 10 ml of the solvent prepared as in (a), referred to hereinafter as solvent (a). Dissolution of the cellulose was complete within 10 minutes at room conditions.

(II) Dissolution tests were repeated for 0.1 g, 0.2 g, 0.3 g, 0.4 g, and 0.5 g portions of crystalline α-cellulose (Avicel), each in 10 ml of solvent (a), by a procedure wherein the cellulose was mixed with solvent at room conditions and then cooled by placing on ice. Times required for complete dissolution to occur are summarized in Table 1.

TABLE 1

| % Avicel in Solvent | Dissolution Time |
| --- | --- |
| 1 | 2 minutes |
| 2 | 2 minutes |
| 3 | 7 minutes |
| 4 | 9 minutes |
| 5 | 15 minutes |

(III) Dissolution tests, performed as described in (II) above, were repeated. In this case, however, amorphous cellulose, instead of crystalline cellulose, was dissolved. Using the same quantities of cellulose, and the same procedures as in (III), the dissolution times summarized in Table 2 were observed.

TABLE 2

| % Cellulose in Solvent | Dissolution Time |
| --- | --- |
| 1 | 2 minutes |
| 2 | 2 minutes |
| 3 | 7 minutes |
| 4 | 9 minutes |
| 5 | 15 minutes |

(IV) Solutions containing greater amounts of cellulose were made by modifying the composition of the solvent and by altering the dissolution procedure. Sodium hydroxide was added to the solvent (a) to give a solution which is 0.5 M in sodium hydroxide. To 1 milliliter of the modified solvent, 300 milligrams Avicel were added, followed by an excess of CdO. Mixing of this solution was carried out resulting in an almost clear, very viscous solution having a cellulose concentration of approximately 30%.

(c) Preparation of Enzyme (I) *Trichoderma viride* cellulase enzyme from the Enzyme Development Corporation, New York, was processed as follows to give an enzyme preparation referred to hereinafter as "CS." Enzyme, 10 g, was added to 25 ml water. Using an ultrafiltration membrane the enzyme solution was concentrated and diluted with excess water and then concentrated to a volume of 25 milliliters again. This was repeated several times until the salt and carbohydrate level of the enzyme preparation was negligible.

(II) Enzyme preparation "CW" was made from the same enzyme as in (c) (I) as follows: Enzyme, 10 gram, was dissolved in 100 milliliters water. Next 57 gram ammonium sulfate was added. Upon mixing, the ammonium sulfate dissolved and a white precipitate formed. This precipitate was separated by centrifugation and redissolved in 30 milliliters of water. The solution was then desalted using Sephadex G-25 (Pharmacia Corporation) and made up to a final volume of about 100 ml.

(d) Hydrolysis of Crystalline α-Cellulose.

(I) To 1 volume of 2% crystalline α-cellulose dissolved in the solvent (a), 2 volumes of 30% HCl were added causing the dissolved cellulose to reprecipitate. This was followed by addition of 5 volumes of sodium acetate buffer and 1 volume enzyme preparation "CS." Upon mixing and incubation at 50° C., up to 50% conversion of cellulose to glucose was obtained in 30 minutes. Apparently the presence of cadmium and ethylene diamine did not inactivate the enzyme.

(II) One volume of 3% Avicel in solvent (a) was mixed with 2.5 volumes water causing the cellulose to reprecipitate. The reprecipitated cellulose was washed with water after which the cellulose concentration was 0.5%. After adjusting the solution to pH 5 with buffer, sufficient enzyme preparation "CW" was added to give an enzyme volume: cellulose weight ratio of 18:1. Incubation of this solution at 50° C. gave 80% conversion to glucose in 5 hours and 90% in 50 hours. In comparison, a control experiment using cellulose which had not been dissolved in solvent and reprecipitated, i.e., untreated cellulose, gave conversions of only 15% after 5 hours and 47% after 50 hours.

EXAMPLE 2

Solvent and enzyme solutions were prepared in accordance with Example 1.

(a) Dissolution of cellulose in corn cob

Corn cobs, ground to 40 mesh size particles, were combined with solvent (a) in a weight ratio of 1:55 corncob:Cadoxen. After stirring for 2.5 hours, the solid and liquid phases were separated. The solid phase was washed with water, dried and weighed. Weight loss, based on initial and final weights of dry solids, was as high as 77%. This indicated all cellulosic material had been dissolved.

(b) Dissolution of cellulose in corn residue

Corn residue, ground to 40 mesh, was combined with solvent in a weight ratio of 1:10 corn residue:Cadoxen. The stirring, washing, and recovering of solids was performed as described in Example 2(a). Weight loss was estimated to be between 44% and 94% (dry basis).

(c) In situ dissolution and hydrolysis of corn residue

Corn residue containing 38% α-cellulose was mixed with Cadoxen in a 1:4.2 weight ratio-corn residue: Cadoxen. After sitting 12 hours, buffer, water, and enzyme preparation "CW" were added to give a 2.5% solution of residue at pH 5. Hydrolysis of the mixture at 45° C. gave 72% conversion of the α-cellulose to glucose in 19 hours. Since the solvent pretreatment and subsequent cellulose reprepicipitation was done without first separating the solvent and dissolved cellulose from the solid residue, this technique was referred to as "in situ" dissolution (and reprecipitation).

(d) In situ dissolution and hydrolysis of bagasse (sugar cane residue)

The bagasse residue containing 33% α-cellulose was mixed with Cadoxen in a 1:4.2 weight ratio-bagasse: Cadoxen. Using the same conditions as in Example 2(c), 70% conversion was obtained in 19 hours.

EXAMPLE 3

Solvent and enzyme solutions were prepared in accordance with Example 1.

(a) Corn residue (10 grams), ground to 40 mesh, is blended in 500 ml of 1 normal $H_2SO_4$. The mixture is heated to boiling in a flask equipped with a condenser for one hour. The mixture is then filtered to separate a solid residue containing mostly cellulose and lignin and a hydrolysate containing predominantly $C_5$ sugars. The solid residue was dried, weighed and combined with solvent (a) in a weight ratio of 1:10 residue: solvent. After stirring for 3 hours, the solid and liquid phases were separated. The solid phase was washed with water, dried and weighed. Weight loss, based on the initial and final weights of dry solids, was as high as 75%. This indicated that all of the cellulose was dissolved in the liquid phase.

(b) The cellulose-containing liquid phase from Example 3(a) is combined with 10 volumes of water causing the dissolved cellulose to reprecipitate. The precipitate is filtered and washed with water to remove excess Cadoxen. The washed precipitate is mixed with 5 volumes of sodium acetate buffer and 1 volume enzyme preparation "CS". Upon mixing and incubation at 50° C. for 30 minutes, 47% conversion of cellulose to glucose is obtained.

(c) The procedure of Example 3(b) is repeated, except that the reprecipitated cellulose is hydrolyzed to glucose using 5 volumes of 3 normal $H_2SO_4$ as the hydrolytic agent. The hydrolysis is carried out by boiling the reprecipitated cellulose in the sulfuric acid solution for 2 hours to obtain a 60% conversion to glucose.

EXAMPLE 4

Hydrolysis with Immobilized Enzyme (a) Preparation of immobilized enzyme

A filter disk of chemically activated porous PVC membrane material (supplied by Amerace Corporation, Butter, N.J.) was submersed in a solution of 10% glutaraldehyde buffered with phosphate to pH 7 for 2 hours at room conditions. After washing with water and sodium acetate buffer (pH 5), the disk was submersed in enzyme preparation "CW" for 12 hours at 4° C. The disk was then washed with buffer, placed in a column apparatus and used as described below.

(b) Hydrolysis of cellulose using immobilized enzyme

Crystalline α-cellulose (Avicel) was mixed with Cadoxen in a 1:6 weight ratio-Avicel: Cadoxen. After sitting 12 hours, the cellulose was reprecipitated by adding a buffer and water. Enzyme preparation "CW" was added to give a 2.5% solution of residue at pH 5. Hydrolysis of the mixture at 45° C. for 20 hours resulted in a complete solubilization of the cellulose to a clear solution with 79% of the cellulose being converted to glucose and the balance to cellodextrins. This clear solution was passed through the immobilized enzyme disk 5 times resulting in an increase in glucose conversion from 79% to 81%. Glucose was formed due to hydrolysis of soluble cellooligosaccharides to glucose. A control study using only soluble enzyme was conducted, consecutively. In this run, glucose conversion stayed constant at 79% during the same time period.

Although certain preferred embodiments of the invention have been disclosed for purpose of illustration, it will be evident that various changes and modification may be made therein without departing from the scope and spirit of the invention set forth in the following claims.

What is claimed is:

1. A process for providing a yield of glucose from a cellulosic material, said process comprising:
   fractionating the cellulosic material into a solid cellulose- and lignin-containing fraction and a liquid fraction containing hemicellulose or $C_5$ sugars derived therefrom;
   treating said solid cellulose- and lignin-containing fraction with a solvent for cellulose to dissolve the cellulose in said fraction and to form a lignin-containing residue;
   reprecipitating the dissolved cellulose; and
   hydrolyzing the reprecipitated cellulose to yield glucose.

2. The process of claim 1, wherein the dissolved cellulose is separated from said lignin-containing residue before being reprecipitated and hydrolyzed to glucose.

3. The process of claim 1, wherein the dissolved cellulose is hydrolyzed to glucose in the presence of said lignin-containing residue, whereafter said residue is separated from the glucose.

4. A process for providing a yield of glucose from a cellulosic material, said process comprising:
   removing hemicellulose from the cellulosic materials;
   dissolving in a solvent for cellulose the cellulosic material having said hemicellulose removed therefrom;
   reprecipitating the dissolved cellulose;
   hydrolyzing the reprecipitated cellulose with an enzyme or acid to yield glucose, and a lignin-containing solid residue; and
   removing the lignin-containing residue from the glucose.

5. A process for providing a high yield of glucose from a cellulosic material, said process comprising:
   reducing the physical size of the cellulosic material to about 5 to 100 mesh;
   treating the cellulosic materials with a dilute acid or alkali to remove hemicellulose therefrom and to form a cellulose- and lignin-containing residue;
   treating said residue with a solvent for cellulose to dissolve the cellulose and thereby form a liquid mixture having lignin therein in solid form,
   precipitating cellulose from said liquid mixture;
   hydrolyzing the precipitated cellulose by addition of acid or cellulase enzyme or a combination thereof to provide a high yield of glucose therefrom; and
   separating the yielded glucose from the solid lignin.

6. A process for recovering cellulose from a cellulosic material and utilization of said recovered cellulose to provide a yield of glucose, said process comprising:
   removing hemicellulose from a cellulosic material;

dissolving in a solvent for cellulose the cellulosic material having said hemicellulose removed therefrom to form a solution substantially comprised of cellulose and solvent and a lignin-containing solid residue;

separating said lignin-containing solid residue from said solution;

reprecipitating cellulose from said solution; and hydrolyzing the reprecipitated cellulose to provide a yield of glucose.

7. The process of claim 6, wherein said cellulose is hydrolyzed by an acid and/or a cellulase enzyme to provide a high yield of glucose.

8. The process of claim 7, wherein said cellulose is hydrolyzed by use of either free or immobilized enzymes.

9. The process of claim 7, wherein said cellulase enzyme is an endo-1, 4-beta-glucanase.

10. The process of claim 9, wherein said cellulase enzyme is *Tricoderma viride* cellulase solution.

11. A process for providing a high yield of glucose from cellulose recovered from a cellulosic material, said process comprising:

treating a cellulosic material with a dilute acid to form a liquid fraction containing primarily $C_5$ sugars and a solid fraction containing primarily cellulose and lignin;

separating said liquid fraction from said solid fraction;

dissolving the cellulose in said solid fraction by contacting said fraction with a solvent, the lignin in said fraction remaining as a solid residue;

separating said solid residue from the dissolved cellulose;

reprecipitating the cellulose from said solvent; and hydrolyzing the reprecipitated cellulose by addition of acid and/or cellulase enzyme to provide a high yield of glucose therefrom.

12. A process for providing a high yield of glucose from cellulose recovered from a cellulosic material, said process comprising:

treating a cellulosic material with a dilute base to form a liquid fraction containing primarily hemicellulose and a solid fraction containing primarily cellulose and lignin;

separating said liquid fraction from said solid fraction;

dissolving the cellulose in said solid fraction by contacting said fraction with a solvent, the lignin in said fraction remaining as a solid residue;

separating said solid residue from the dissolved cellulose;

reprecipitating the cellulose from said solvent; and hydrolyzing the reprecipitated cellulose by addition of acid and/or cellulase enzyme to provide a high yield of glucose therefrom.

13. A process for recovering cellulose from a cellulosic material, said process comprising:

removing hemicellulose from a cellulosic material;

dissolving in a solvent for cellulose the cellulosic material having said hemicellulose removed therefrom;

separating lignin from the cellulosic material dissolved in said solvent such that a solution substantially of cellulose and solvent remains;

reprecipitating cellulose from said solution; and recovering the reprecipitated cellulose in solid form.

14. The process of claim 13, wherein said process includes physically reducing the cellulosic material in size before removing said hemicellulose therefrom.

15. The process of claim 13, wherein said hemicellulose is removed by extraction with a dilute acid or alkali.

16. The process of claim 13, wherein the cellulosic material is dissolved in a solvent comprising from about 25–30% by weight of ethylenediamine, from about 70–75% by weight water, and from about 4.5–7% by weight of cadmium added as oxide or hydroxide.

17. The process of claim 13, wherein said solvent is recovered for reuse.

* * * * *